(12) United States Patent
Liu et al.

(10) Patent No.: US 10,765,382 B2
(45) Date of Patent: Sep. 8, 2020

(54) METHOD FOR MIXED TRACERS DYNAMIC PET CONCENTRATION IMAGE RECONSTRUCTION BASED ON STACKED AUTOENCODER

(71) Applicant: ZHEJIANG UNIVERSITY, Hangzhou, Zhejiang Province (CN)

(72) Inventors: Huafeng Liu, Hangzhou (CN); Dongsheng Ruan, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 93 days.

(21) Appl. No.: 15/745,003

(22) PCT Filed: Jul. 13, 2017

(86) PCT No.: PCT/CN2017/092755
§ 371 (c)(1),
(2) Date: Jan. 15, 2018

(87) PCT Pub. No.: WO2018/129891
PCT Pub. Date: Jul. 19, 2018

(65) Prior Publication Data
US 2019/0008468 A1    Jan. 10, 2019

(51) Int. Cl.
*A61B 6/03* (2006.01)
*G01T 1/29* (2006.01)
(Continued)

(52) U.S. Cl.
CPC ............ *A61B 6/037* (2013.01); *G01R 33/481* (2013.01); *G01T 1/2985* (2013.01);
(Continued)

(58) Field of Classification Search
CPC .... A61B 6/037; G01R 33/481; G01T 1/2985; G06T 5/002; G06T 11/003; G06T 7/0012
See application file for complete search history.

(56) References Cited

U.S. PATENT DOCUMENTS 7,848,557 B2 * 12/2010 Kadrmas ............... G01T 1/1611
378/4
2016/0000945 A1    1/2016 Nedergaard et al.

FOREIGN PATENT DOCUMENTS

CN    103295207        9/2013
CN    103295207 A  *  9/2013
(Continued)

OTHER PUBLICATIONS

Motomura et al., "Improved imaging performance of a semiconductor Compton camera GREI", May 3, 2013, Journal of Analytical Atomic Spectrometry, vol. 28, Iss. 6, pp. 934-939 (Year: 2013).*
(Continued)

*Primary Examiner* — David P Porta
*Assistant Examiner* — Jeremy S Valentiner
(74) *Attorney, Agent, or Firm* — Jiwen Chen

(57) ABSTRACT

The present invention discloses a method for reconstructing dynamic PET concentration distribution image of dual-tracer based on stacked autoencoder. The invention introduces deep learning into dynamic tracer PET concentration distribution image reconstruction, and the process is mainly divided into two stages of training and reconstruction. In the training phase, train multiple autoencoders using the concentration distribution images of mixed tracers taken as input, and the concentration distribution images of the two tracers taken as labels to build the stacked autoencoder. In the reconstruction phase, the concentration distribution images of the individual tracer can be reconstructed by inputting the concentration distribution images of the mixed traces to the well trained stacked autoencoder. The present invention realizes the reconstruction of the dynamic PET concentration distribution images of mixed tracers from the data-driven point of view, and effectively solves the prob-
(Continued)

lems of poor reconstruction effect and inability of simultaneous injection.

6 Claims, 3 Drawing Sheets

(51) Int. Cl.
*G01R 33/48* (2006.01)
*G06T 11/00* (2006.01)
*G06N 3/04* (2006.01)
*G06N 3/08* (2006.01)
*G06T 5/00* (2006.01)
*G06T 7/20* (2017.01)
*G06T 7/00* (2017.01)

(52) U.S. Cl.
CPC ........... *G06N 3/0454* (2013.01); *G06N 3/084* (2013.01); *G06T 11/003* (2013.01); *G06T 11/006* (2013.01); *G06T 5/002* (2013.01); *G06T 7/0012* (2013.01); *G06T 7/20* (2013.01); *G06T 2207/10104* (2013.01); *G06T 2210/41* (2013.01); *G06T 2211/412* (2013.01)

(56) References Cited

FOREIGN PATENT DOCUMENTS

| CN | 105678821 | | 6/2016 | |
| CN | 105678821 A | * | 6/2016 | |
| CN | 105894550 | | 8/2016 | |
| CN | 107133997 A | * | 9/2017 | ............. G06T 11/00 |
| WO | WO-2014172927 A1 | * | 10/2014 | |

OTHER PUBLICATIONS

Goorden et al., VECTor: A Preclinical Imaging System for Simultaneous Submillimeter SPECT and PET, Feb. 2013, vol. 54, No. 2, pp. 306-312 (Year: 2013).*
Liu et al.—CN 105678821 A—English Translation obtained from Google Patents Sep. 23, 2019 (Year: 2019).*
Liu et al.—CN 103295207 A—English Translation obtained from Google Patents Sep. 23, 2019 (Year: 2019).*
Zabalza et al., Novel segmented stacked autoencoder for effective dimensionality reduction and feature extraction in hyperspectral imaging, Apr. 2016, Neurocomputing, vol. 185, pp. 1-10 (Year: 2016).*
Zabalza, Novel segmented stacked autoencoder for effective dimensionality reduction and feature extraction in hyperspectral imaging, Apr. 2016, Neurocomputing, vol. 185, pp. 1-10 (Year: 2016).*
Cui et al., Deep Reconstruction Model for Dynamic PET Images, Sep. 21, 2017, PLoS ONE Journal, vol. 12, Iss. 9, pp. 1-21 (Year: 2017).*
Liu et al.—CN 107133997 A—English Translation obtained from Google Patents on Mar. 27, 2020 (Year: 2020).*

* cited by examiner

METHOD FOR MIXED TRACERS DYNAMIC PET CONCENTRATION IMAGE RECONSTRUCTION BASED ON STACKED AUTOENCODER

This is a U.S. national stage application of PCT Application No. PCT/CN2017/092755 under 35 U.S.C. 371, filed Jul. 13, 2017 in Chinese, claiming priority of Chinese Application No. 201710029109.1, filed Jan. 16, 2017, all of which are hereby incorporated by reference.

TECHNICAL FIELD

The present invention belongs to the field of PET imaging, and relates to a method for reconstructing dynamic mixed tracers PET concentration distribution images based on stacked autoencoder.

BACKGROUND

Positron emission tomography (PET) is one of the important methods of nuclear medicine imaging. It is widely used in other fields such as oncology and neurology, and plays a very important role in medical research and clinical diagnosis. PET can observe the cellular metabolic activity at the molecular level and provide an effective basis for the early diagnosis and prevention of the disease. In the process of PET imaging, the tracer decays in the tissues of the human body. The positrons generated during the decay react annihilate with negative electrons to generate a pair of gamma photons with energy of 511 kev in opposite directions. The photons are recorded by the ring probe to generate projection data. The inversion of projection data by some mathematical methods can reconstruct the spatial concentration distribution of tracer in the human body.

In order to obtain more patient's physiological information, mixed tracers imaging has become a hot topic in PET imaging research. Traditional methods require individual injections, independent scans, and independent imaging for each tracer, which undoubtedly increases the patient's time, expense, and safety concerns. Therefore, double injection-single scan is a more reasonable technique for processing PET mixed tracer imaging. However, since each tracer decay produces gamma photons with energy of 511 keV, it is impossible to directly separate the counting photons generated by each tracer in hardware.

Traditionally, the methods of direct fitting and kinetic parameter estimation are often used for the image reconstruction of mixed tracers PET concentration distribution. The former method mainly uses some mathematical methods to directly fit the time activity curve (TAC). Although the calculation speed is fast, the reconstructed image quality is poor. The latter approach incorporates a compartment model and is computationally complex by estimating the k parameters to fit the TAC curve. In addition, these algorithms require an interval (10-20 minutes) between two tracer injection times, and the TAC curve for the second tracer can be obtained by analyzing and calculating the TAC curve for first tracer. In other words, these algorithms are not suitable for reconstructing PET concentration distribution image in the case of simultaneous injection.

SUMMARY OF THE INVENTION

In view of the above technical problems, the present invention provides a method for reconstructing dynamic PET concentration distribution images of mixed tracers based on stacked autoencoder, which can reconstruct the PET concentration distribution images of each tracer with simultaneous injection of two tracers.

A method for reconstructing mixed tracers dynamic PET concentration distribution images based on stacked autoencoder comprises the following steps:

(1) The two tracers are injected into the biological tissue, the detector is used to detect the biological tissue with radiopharmaceuticals, and the coincidence counting vector corresponding to different time is collected to construct the coincidence counting matrix Y for mixed tracers, $Y_1$ for the first tracer and $Y_2$ for the second tracer.

(2) According to the coincidence counting matrices Y, $Y_1$ and $Y_2$, the dynamic PET concentration distribution images X for the mixed tracers, $X_1$ for the first tracer and $X_2$ for the second tracer are obtained by the ML-EM algorithm using the principle of PET imaging;

Then the PET concentration distribution images of different frames are arranged in pixel order to obtain the dynamic concentration truth vector set x for the mixed tracer PET images and the dynamic concentration truth vector set o for two combined tracers. x and o are taken as the training set;

$$\begin{cases} x = [x_1, x_2, \ldots, x_{m \times m}] \\ o = [o_1, o_2, \ldots, o_{m \times m}] \end{cases}$$

wherein each vector in x is used as the input of the neural network and each vector in o is used as the truth label;

(3) Training multiple autoencoders with training set. Well trained autoencoders are cascaded to stacked autoencoder, and then fine-tune the stacked autoencoder with the training set to obtain PET concentration distribution image reconstruction model;

(4) The new coincidence counting matrix is acquired by the method of step (1), then the dynamic mixed PET concentration distribution images of the new mixed tracers are obtained according to the step (2) and the obtained PET concentration distribution images in different frames are arranged in pixel order as a test set. Finally the test set is input into the PET concentration distribution image reconstruction model to reconstruct the dynamic PET concentration distribution images of the individual tracer.

In step (1), the mixed tracers are obtained by mixing a plurality of tracers. In the present invention, the mixed tracers are obtained from two kinds of tracers.

In step (2), the PET imaging principle is based on the following relationship:

$Y = GX + \text{noise}$ wherein G is the system matrix, Y is the coincidence count matrix, X is the PET concentration distribution image and noise is the measurement noise matrix. The measurement noises include the reflection coincidence events and the scattering coincidence events.

In step (2), the method for arranging the PET concentration distribution images with different frames in pixel order is as follows:

First, the pixel data in the dynamic PET concentration distribution images X, $X_1$ and $X_2$, are arranged in the following form:

$$\begin{cases} x = [x_1, x_2, \ldots, x_i, \ldots, x_{m \times m}] \\ x^1 = [x_1^1, x_2^1, \ldots, x_i^1, \ldots, x_{m \times m}^1] \\ x^2 = [x_1^2, x_2^2, \ldots, x_i^2, \ldots, x_{m \times m}^2] \end{cases}$$

wherein $x^1$ is the dynamic concentration truth vector set of pixel points for the first tracer PET concentration distribution image, $x^2$ is the dynamic concentration truth vector set of pixel points for the second tracer PET concentration distribution image, $x_i$ is the dynamic concentration truth vector of the i-th pixel in the mixed tracers PET concentration distribution images, $x_i^1$ and $x_i^2$ are respectively the dynamic concentration truth vectors of the i-th pixel in the PET concentration distribution images of the first tracer and the second tracer; i is a natural number and $1 \leq i \leq m^2$, m×m is the resolution of the image. $x_i$, $x_i^1$ and $x_i^2$ are expressed as follows:

$$\begin{cases} x_i = [x_{1i}, x_{2i}, \ldots, x_{ji}, \ldots, x_{ki}]^T \\ x_i^1 = [x_{1i}^1, x_{2i}^1, \ldots, x_{ji}^1, \ldots, x_{ki}^1]^T \\ x_i^2 = [x_{1i}^2, x_{2i}^2, \ldots, x_{ji}^2, \ldots, x_{ki}^2]^T \end{cases}$$

wherein $x_{ji}$ is the concentration value of the i-th pixel in the PET concentration distribution image corresponding to the j-th frame of the mixed tracers and $x_{ji}^1$ and $x_{ji}^2$ are respectively the concentration value of i-th pixel in the PET concentration distribution images of j th frame of the first tracer and the second tracer. j is a natural number and $1 \leq j \leq k$. k is the number of PET concentration distribution images for each tracer. $^T$ represents transpose.

Then $x^1$ and $x^2$ are combined to get o, and the i-th vector in o is $$o_i = \begin{bmatrix} x_i^1 \\ x_i^2 \end{bmatrix}_\circ$$

In step (3), the stacked autoencoder consists of input layer, hidden layer and output layer. The input layer to the hidden layer is called the encoder, and the hidden layer to the output layer is called the decoder. The hidden layer of the previous autoencoder is the input layer of the latter autoencoder. For any self-encoder, the number of neurons in the hidden layer is less than the number of neurons in the input layer.

The function model of the autoencoder is as follows:

$$h = f(Wx + b)$$

$$p = f(W'h + b')$$

wherein x, h, and p are respectively the input, hidden, and output layers of the autoencoder, W and b are respectively the weight and bias of encoder, W' and b' are respectively the weight and bias of the decoder. f is the activation function.

In step (3), the method of training stacked autoencoder is as follows:

(3-1) Training the first autoencoder in stacked autoencoder: x in the training set is taken as the input layer of the autoencoder and the minimum of the loss function L between the output layer and the input layer is taken as the target to obtain the model parameters by backpropagation algorithm and gradient descent algorithm;

(3-2) Training any autoencoder in stacked autoencoder except for the first and last ones: the hidden layer of previous autoencoder is taken as the input layer of the autoencoder and the minimum of the loss function L between the output layer and the input layer is taken as the target to obtain the model parameters by backpropagation algorithm and gradient descent algorithm;

(3-3) Training last autoencoder in stacked autoencoder: the hidden layer of previous autoencoder is taken as the input layer of the autoencoder and the minimum of the loss function L' between the output layer and o in training set is taken as the target to obtain the model parameters by backpropagation algorithm and gradient descent algorithm;

(3-4) Training the stacked autoencoder again using the training set of x and o as input and label of stacked autoencoder to obtain PET concentration distribution image reconstruction model.

The loss functions L and L' of stack autoencoder is expressed as:

$$L = \|z - t\|^2 \quad L' = \|o - t\|^2$$

wherein o is the truth label of the training sample.

In step (4), the test set $\hat{x}$ is input to the concentration distribution image reconstruction model to reconstruct the dynamic PET concentration distribution images of two tracers. The specific process is as follows:

First, each column in the test set $\hat{x} = [\hat{x}_1, \hat{x}_2, \ldots, \hat{x}_{m \times m}]$ is used as the input of stacked autoencoder to obtain the output:

$$\hat{o} = [\hat{o}_1, \hat{o}_2, \ldots, \hat{o}_{m \times m}]$$

Then $\hat{o}$ is decomposed into $\hat{x}^1 = [\hat{x}_1^1, \hat{x}_2^1, \ldots, \hat{x}_{m \times m}^1]$ and $\hat{x}^2 = [\hat{x}_1^2, \hat{x}_2^2, \ldots, \hat{x}_{m \times m}^2]$ to reconstruct dynamic tracer PET concentration distribution images of two tracers.

The invention introduces deep learning into dynamic tracer PET concentration distribution image reconstruction, and the process is mainly divided into two stages of training and reconstruction. In the training phase, train multiple autoencoders using the concentration distribution images of mixed tracers taken as input, and the concentration distribution images of the two tracers taken as labels to build the stacked autoencoder. In the reconstruction phase, the concentration distribution images of the individual tracer can be reconstructed by inputting the concentration distribution images of the mixed traces to the well trained stacked autoencoder.

The present invention realizes the reconstruction of the dynamic PET concentration distribution images of mixed tracers from the data-driven point of view, and effectively solves the problems of poor reconstruction effect and inability of simultaneous injection.

DESCRIPTION OF THE PREFERRED EMBODIMENTS

In order to describe the present invention in more detail, the technical solutions of the present invention are described in detail below with reference to the accompanying drawings and specific embodiments.

Figure 1:
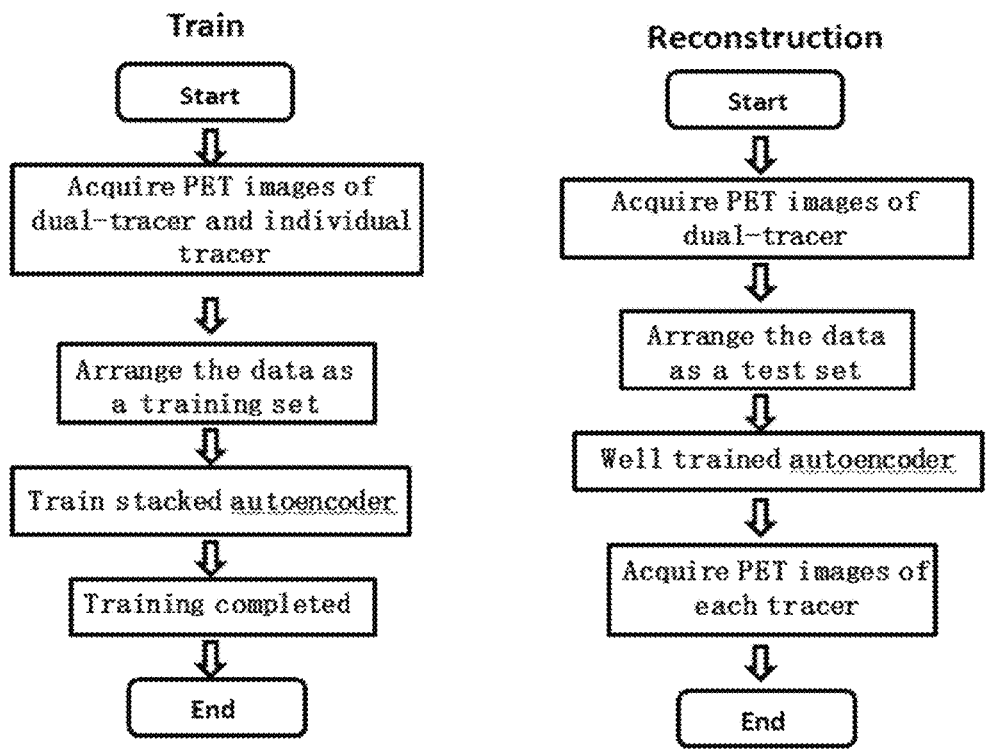
FIG. 1 is an overall framework of the present invention.

The method for reconstructing dynamic PET concentration distribution images based on stacked autoencoder of the present invention is shown in FIG. 1, and specifically comprises the following steps:

S1. The coincidence counting matrix y of mixed tracers and the coincidence counting matrixes $y^1$ and $y^2$ of tracer 1 and tracer 2 are simulated by the principle of dynamic PET detection;

S2. The PET concentration distribution image matrix X of mixed tracers, the PET concentration distribution image matrix X of tracer 1 and the PET concentration distribution image matrix $X^2$ of the tracer 2 were reconstructed from the ML-EM algorithm;

S3. The PET concentration distribution images of X, $X^1$ and $X^2$ are processed: First, the PET concentration distribution images of the three images are arranged in pixel order in the following form:

$$\begin{cases} x = [x_1, x_2, \ldots, x_{m\times m}] \\ x^1 = [x_1^1, x_2^1, \ldots, x_{m\times m}^1] \\ x^2 = [x_1^2, x_2^2, \ldots, x_{m\times m}^2] \end{cases}$$

wherein $$\begin{cases} x_i = [x_{1i}, x_{2i}, \ldots, x_{ki}]^T \\ x_i^1 = [x_{1i}^1, x_{2i}^1, \ldots, x_{ki}^1]^T \\ x_i^2 = [x_{1i}^2, x_{2i}^2, \ldots, x_{ki}^2]^T \end{cases}$$

Then the PET concentration distribution images $x_i^1$ and $x_i^2$ for both tracers are combined into:

$$o_i = [x_i^1 x_i^2] = [x_{1i}^1, x_{2i}^1, \ldots, x_{ki}^1, x_{1i}^2, x_{2i}^2, \ldots, x_{ki}^2]^T$$

o consists of the set of o:

$$o = [o_1, o_2, \ldots, o_{m\times m}]$$

S4. Set the learning rate and training threshold, the number of hidden layer nodes n, l, t of each autoencoder, the number of layers S of stacked autoencoder, the weight parameters W and W' of each autoencoder, and the bias b.

S5. Build a number of autoencoders and update weight parameters W, W' and the bias parameter b by backpropagation algorithm and gradient descent algorithm. x is taken as the input data from the first encoder. o is taken as the output layer of the true value.

Figure 2:
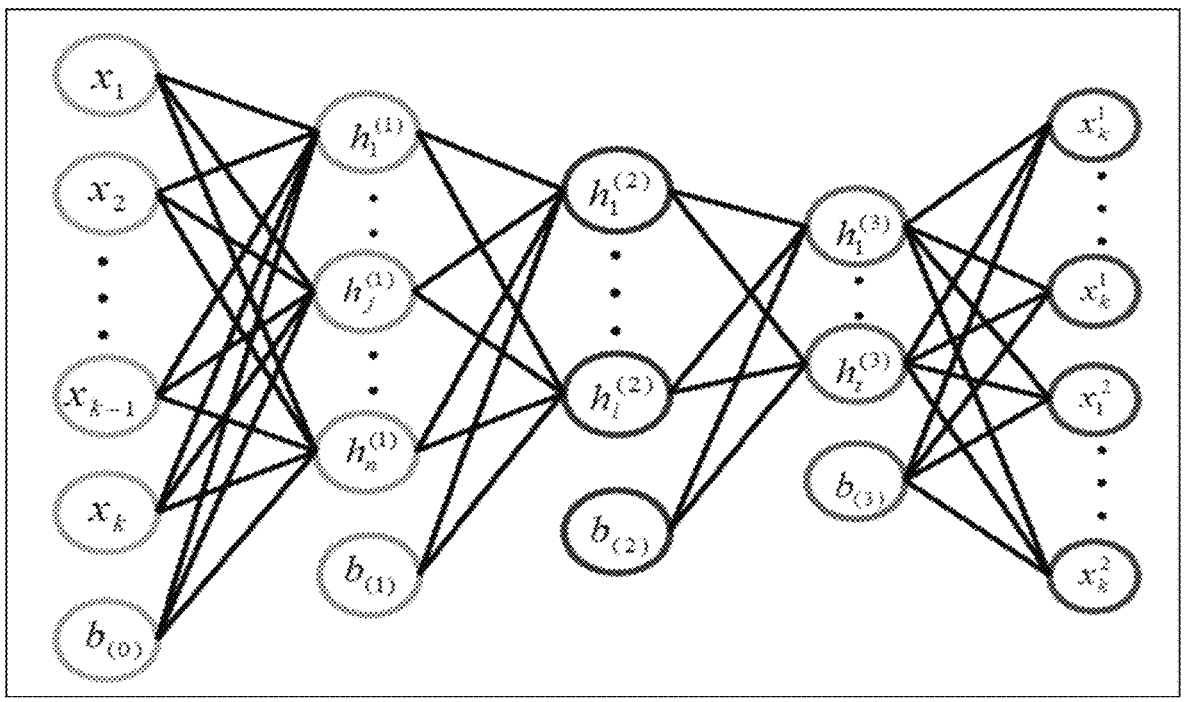
FIG. 2 is a diagram of stacked autoencoder cascaded multiple autoencoders.

S6. The well trained autoencoder concatenated together to get a stacked autoencoder, as shown in FIG. 2, and then x and o are taken as input and output of the stacked autoencoder to train the stacked autoencoder again. The weight parameters W, W' and the bias parameter b are fine-tuned to obtain a PET concentration distribution image reconstruction model of mixed tracers.

S7. Given the emission data $\hat{y}$ of the new mixed tracers, the PET concentration distribution image matrix is solved according to the ML-EM algorithm, and then the PET concentration distribution images are rearranged into $\hat{x} = [\hat{x}_1, \hat{x}_2, \ldots, \hat{x}_{m\times m}]$ in pixel order.

S8. Each column in $\hat{x} = [\hat{x}_1, \hat{x}_2, \ldots, \hat{x}_{m\times m}]$ is input into the PET concentration distribution image reconstruction model of the mixed tracers to obtain an estimate $\hat{o} = [\hat{o}_1, \hat{o}_2, \ldots, \hat{o}_{m\times m}]$. Finally $\hat{o}$ is rearranged into $\hat{x}^1 = [\hat{x}_1^1, \hat{x}_2^1, \ldots, \hat{x}_{m\times m}^1]$ and $\hat{x}^2 = [\hat{x}_1^2, \hat{x}_2^2, \ldots, \hat{x}_{m\times m}^2]$, i.e. PET concentration distribution images for both tracers.

The accuracy of the present invention is verified using thorax phantom simulation dat. The computer configuration used in this experiment: 8G memory, 3.40 GHz, 64-bit operating system and CPU for Intel i7-6700. The tracers are set to $^{18}$F-FDG and $^{11}$C-acetate.

Here, we respectively simulate four different sampling times. Each sampling time is divided into three different sampling intervals. Different degrees of Poisson noise are added to each sample interval data as shown in Table 1 below:

TABLE 1

| sampling time | sampling interval |
|---|---|
| 40 min | 8*30 s 13*60 s 4*120 s 3*300 s |
| | 10*24 s 10*48 s 4*120 s 4*200 s |
| | 8*30 s 10*60 s 6*100 s 4*240 s |
| 50 min | 5*24 s 13*50 s 8*60 s 5*180 s 4*300 s |
| | 12*30 s 6*60 s 4*120 s 6*300 s |
| | 10*18 s 6*60 s 5*120 s 4*240 s 3*300 s |
| 60 min | 4*30 s 10*60 s 4*120 s 10*240 s |
| | 10*36 s 6*60 s 6*180 s 6*300 s |
| | 10*30 s 5*60 s 5*120 s 4*240 s 4*360 s |
| 70 min | 6*40 s 8*60 s 4*120 s 10*240 s |
| | 4*30 s 10*60 s 6*180 s 8*300 s |
| | 4*30 s 10*60 s 4*120 s 10*300 s |

We added poisson noise levels of 1%, 2%, 4%, 5%, 6%, 8%, 9%, 11% and 16% in the above data. The data of 1%, 4%, 5%, 8%, 11% and 16% noise levels are used as the training set and the data of 2%, 6% and 9% noise levels are used as the test set. The resolution of the PET concentration distribution image is 128×128 and the total number of frames is 28 frames. The main evaluation indicators include Bias and Variance:

$$\text{Bias} = \frac{1}{n}\sum_{i=1}^{n}\left(\frac{u_i - \hat{u}_i}{\hat{u}_i}\right)$$

$$\text{Variance} = \frac{1}{n}\sum_{i=1}^{n}\left(\frac{u_i - \bar{u}_n}{\bar{u}_i}\right)^2$$

wherein $u_i$, $\hat{u}_i$, $\bar{u}_n$ represent the true value of the i-th pixel, the estimated value of the i-th pixel, and the average pixel estimation value, respectively. Table 2 shows the reconstruction of the two tracers at different frame. The sampling time is 50 minutes and sampling interval 10*18 s, 6*60 s, 5*120 s, 4*240 s and 3*300 s.

TABLE 2

| frame | 1 | 4 | 8 | 13 | 17 | 22 |
|---|---|---|---|---|---|---|
| | | | $^{18}$F-FDG | | | |
| Bias (noise 2%) | 0.0703 | 0.0075 | 0.0226 | 0.0128 | 0.0079 | 0.0072 |
| Bias (noise 6%) | 0.1021 | 0.0097 | 0.0308 | 0.0193 | 0.0101 | 0.0074 |
| Bias (noise 9%) | 0.1288 | 0.0120 | 0.0379 | 0.0247 | 0.0122 | 0.0081 |
| Variance (noise 2%) | 0.0069 | 0.0005 | 0.0010 | 0.0006 | 0.0006 | 0.0007 |

TABLE 2-continued

| frame | 1 | 4 | 8 | 13 | 17 | 22 |
|---|---|---|---|---|---|---|
| Variance (noise 6%) | 0.0128 | 0.0005 | 0.0016 | 0.0009 | 0.0006 | 0.0007 |
| Variance (noise 9%) | 0.0192 | 0.0006 | 0.0022 | 0.0012 | 0.0006 | 0.0006 |
| $^{11}$C-acetate | | | | | | |
| Bias (noise 2%) | 0.1063 | 0.0126 | 0.0075 | 0.0102 | 0.0117 | 0.0077 |
| Bias (noise 6%) | 0.1580 | 0.0167 | 0.0081 | 0.0152 | 0.0178 | 0.0106 |
| Bias (noise 9%) | 0.2012 | 0.0202 | 0.0089 | 0.0195 | 0.0229 | 0.0133 |
| Variance (noise 2%) | 0.0153 | 0.0007 | 0.0006 | 0.0007 | 0.0006 | 0.0004 |
| Variance (noise 6%) | 0.0302 | 0.0008 | 0.0006 | 0.0008 | 0.0009 | 0.0005 |
| Variance (noise 9%) | 0.0468 | 0.0009 | 0.0006 | 0.0010 | 0.0010 | 0.0005 |

It can be seen from Table 2 that in the case of noise level, the reconstructed deviations are less than 0.3 and the variance is less than 0.05. Therefore, the present invention can well reconstruct the PET concentration distribution images of the two tracers. Meanwhile, the higher the noise is, the worse the rebuilding effect is.

Figure 3:
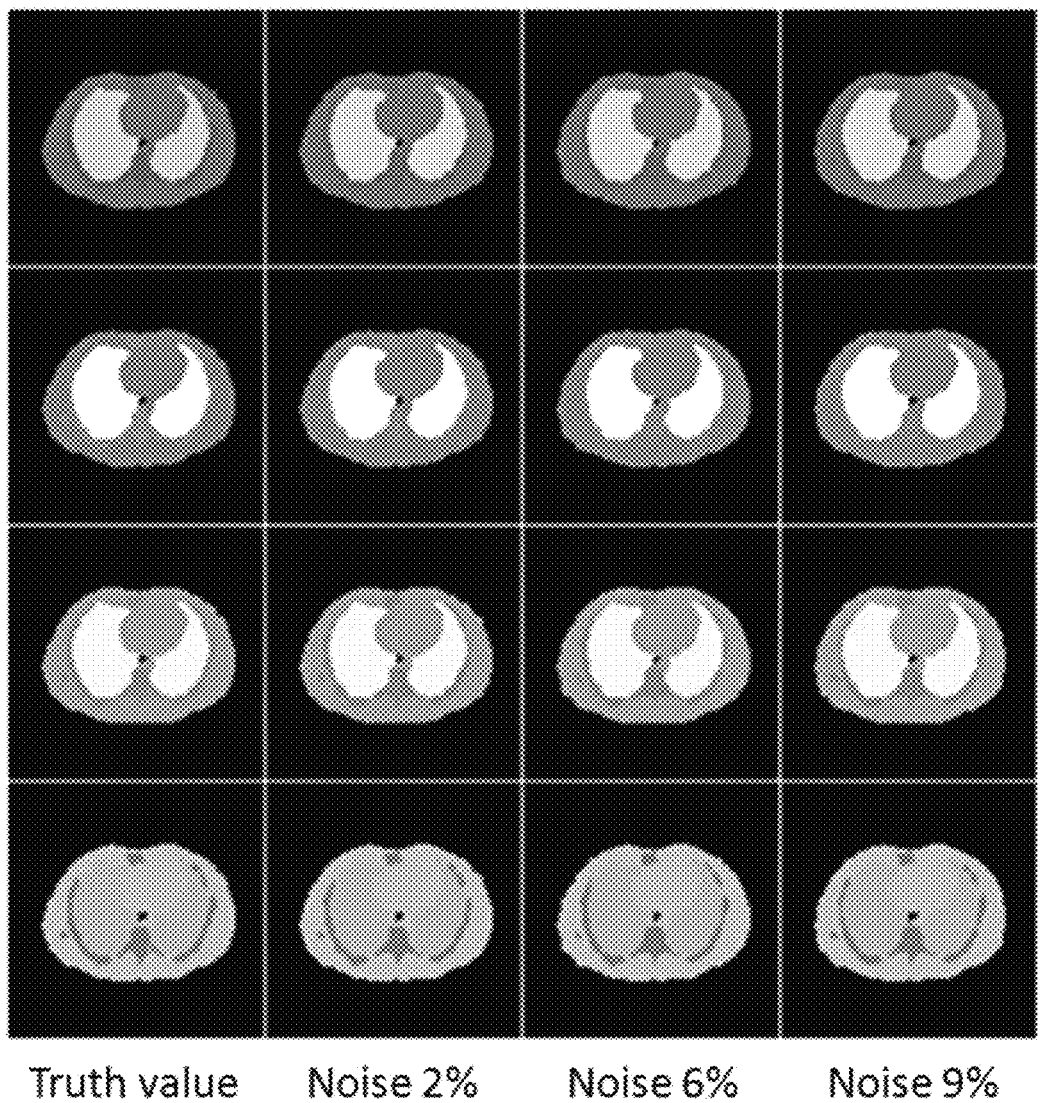
FIG. 3 shows the reconstruction results of the third frame of tracer $^{18}$F-FDG.
Figure 4:
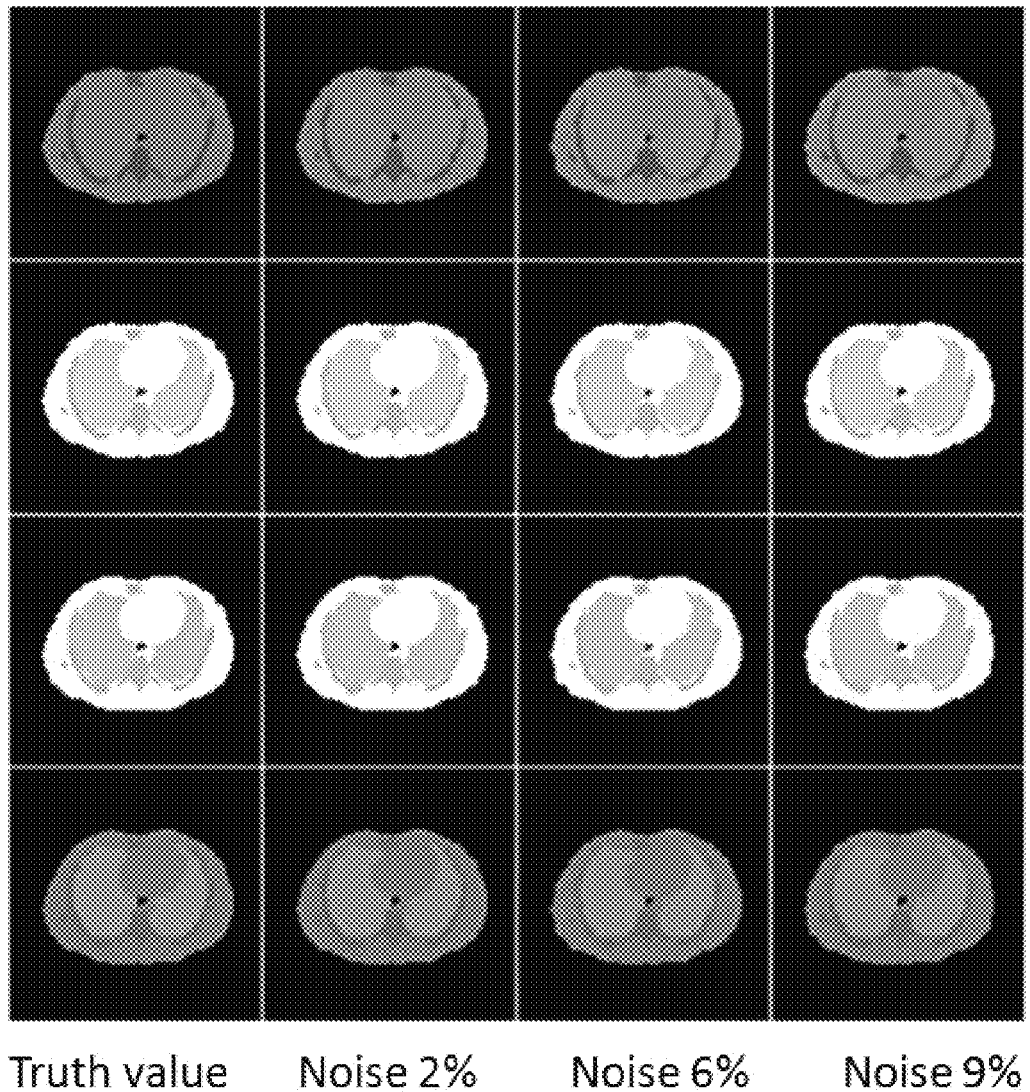
FIG. 4 shows the reconstruction results of the third frame of tracer $^{11}$C-acetate.

FIGS. 3 and 4 show the comparison of the reconstruction results of two tracers and true values at different sampling times and intervals, where the first column is true value and the latter three columns are reconstructed results at different noise levels. The first row is 40 minutes, the second row is 50 minutes, the third row is 60 minutes and the fourth row is 70 minutes. The first sampling interval is used in Table 1. FIGS. 3 and 4 show the reconstruction of the third frame of tracers $^{18}$F-FDG and $^{11}$C-acetate, respectively. From both figures, it can be seen that the PET concentration distribution image reconstructed by the present invention is very effective and can effectively solve the problem that the dual-tracer cannot be injected simultaneously and the reconstruction effect is poor.

The technical solutions and beneficial effects of the present invention have been described in detail in the above specific embodiments. It should be understood that the above is only the most preferred embodiments of the present invention and not intended to limit the present invention. Any modification, supplement and equivalent replacement made within the principle of the present invention should be included in the protection scope of the present invention.

The invention claimed is:

1. A method for reconstructing mixed tracers dynamic position emission tomography (PET) concentration distribution images based on stacked autoencoder comprising the following steps:

(1) injecting a first tracer and a second tracer into a biological tissue, detecting the biological tissue by using a pair of detectors, and collecting coincidence counting vectors corresponding to different collection time to construct a coincidence counting matrix Y for the first tracer and the second tracer, a coincidence counting matrix $Y_1$ for the first tracer and a coincidence counting matrix $Y_2$ for the second tracer;

(2) according to the coincidence counting matrices Y, $Y_1$ and $Y_2$, obtaining dynamic PET concentration distribution images X for the first tracer and the second tracer, dynamic PET concentration distribution images $X^1$ for the first tracer and dynamic PET concentration distribution images $X^2$ for the second tracer by maximum likelihood-expectation maximization (ML-EM) algorithm using a principle of PET imaging;

then arranging the PET concentration distribution images of different frames in pixel order to obtain a dynamic concentration truth vector set x for the first tracer and the second tracer PET images X, and a dynamic concentration truth vector set o for PET images $X^1$ and $X^2$ after the first tracer and the second tracer are combined, x and o being taken as a training set;

$$\begin{cases} x = [x_1, x_2, \cdots, x_{m \times m}] \\ o = [o_1, o_2, \cdots, o_{m \times m}] \end{cases}$$

wherein each vector in x is used as an input of a neural network and each vector in o is used as a truth label;

(3) training multiple autoencoders with the training set, cascading trained autoencoders to the stacked autoencoder, and then fine-tuning the stacked autoencoder with the training set to obtain PET concentration distribution image reconstruction model, wherein the stacked autoencoder consists of an input layer, a hidden layer and an output layer, the input layer to the hidden layer is called an encoder, and the hidden layer to the output layer is called a decoder, the hidden layer of a previous autoencoder is the input layer of a latter autoencoder; for any self-encoder, the number of neurons in the hidden layer is less than the number of neurons in the input layer;

(4) repeating the method of the step (1) and using new mixed tracers to acquire a new coincidence counting matrix, then obtaining the dynamic mixed PET concentration distribution images of the new mixed tracers according to the step (2) and arranging the obtained PET concentration distribution images in different frames in pixel order as a test set, inputting the test set into the PET concentration distribution image reconstruction model to reconstruct the dynamic PET concentration distribution images of the first tracer and the second tracer, respectively.

2. The method for reconstructing dynamic PET concentration distribution images based on stacked autoencoder with mixed tracers according to claim 1 characterized in that: the method for arranging PET concentration distribution images of different frames in pixel order is as follows: first, the pixel data in the dynamic PET concentration distribution images X, $X^1$ and $X^2$ are arranged in the following form:

$$\begin{cases} x = [x_1, x_2, \ldots, x_i, \ldots, x_{m \times m}] \\ x^1 = [x_1^1, x_2^1, \ldots, x_i^1, \ldots, x_{m \times m}^1] \\ x^2 = [x_1^2, x_2^2, \ldots, x_i^2, \ldots, x_{m \times m}^2] \end{cases}$$

wherein $x^1$ is the dynamic concentration truth vector set of pixel points for the first tracer PET concentration distribution image, $x^2$ is the dynamic concentration truth vector set of pixel points for the second tracer PET concentration distribution image, x is the dynamic concentration truth vector of the i-th pixel in the mixed tracers PET concentration distribution images, x, and x, are respectively the dynamic concentration truth vectors of the i-th pixel in the PET concentration distribution images of the first tracer and the second tracer; i is a natural number and $1 \leq i \leq m^2$, m×m is the resolution of the image, x, x and xj are expressed as follows:

$$\begin{cases} x_i = [x_{1i}, x_{2i}, \ldots, x_{ji}, \ldots, x_{ki}]^T \\ x_i^1 = [x_{1i}^1, x_{2i}^1, \ldots, x_{ji}^1, \ldots, x_{ki}^1]^T \\ x_i^2 = [x_{1i}^2, x_{2i}^2, \ldots, x_{ji}^2, \ldots, x_{ki}^2]^T \end{cases}$$

wherein x, is the concentration value of the i-th pixel in the PET concentration distribution image corresponding to the j-th frame of the mixed tracers and $x^1$ and $x^2$ are respectively the concentration value of i-th pixel in the PET concentration distribution images of j th frame of the first tracer and the second tracer, j is a natural number and $1 \leq j \leq k$, k is the number of PET concentration distribution images for each tracer, $^T$ represents transpose;

then $x^1$ and $x^2$ are combined to get o, and the i-th vector in o is $$o_i = \begin{bmatrix} x_i^1 \\ x_i^2 \end{bmatrix}.$$

3. The method for reconstructing dynamic mixed tracers PET concentration distribution images based on stacked autoencoder according to claim 1 characterized in that: the function model of the autoencoder is as follows:

$$h = f(Wx+b)$$

$$p = f(W'h+b')$$

wherein x, h, and p are respectively the input, hidden, and output layers of the autoencoder, W and b are respectively the weight and bias of encoder, W' and b' are respectively the weight and bias of the decoder, f is the activation function.

4. The method for reconstructing dynamic mixed tracers PET concentration distribution images based on stacked autoencoder according to claim 3 characterized in that: in step (3), the specific method of training stacked autoencoder is as follows:

(3-1) training the first autoencoder in stacked autoencoder: x in the training set is taken as the input layer of the autoencoder and the minimum of the loss function L between the output layer and the input layer is taken as the target to obtain the model parameters by backpropagation algorithm and gradient descent algorithm;

(3-2) training any autoencoder in stacked autoencoder except for the first and last ones: the hidden layer of previous autoencoder is taken as the input layer of the autoencoder and the minimum of the loss function L between the output layer and the input layer is taken as the target to obtain the model parameters by backpropagation algorithm and gradient descent algorithm;

(3-3) training last autoencoder in stacked autoencoder: the hidden layer of previous autoencoder is taken as the input layer of the autoencoder and the minimum of the loss function L' between the output layer and o in training set is taken as the target to obtain the model parameters by backpropagation algorithm and gradient descent algorithm;

(3-4) training the stacked autoencoder again using the training set of x and o as input and label of stacked autoencoder to obtain PET concentration distribution image reconstruction model.

5. The method for reconstructing dynamic mixed tracers PET concentration distribution images based on stacked autoencoder according to claim 4 characterized in that: the loss functions L and L' of the stack autoencoder is expressed as:

$$L = \|z-t\|^2 \quad L' = \|o-t\|^2$$

wherein o is the truth label of the training sample, z is an input of the stacked autoencoder and t is an output of the stacked autoencoder.

6. The method for reconstructing dynamic mixed tracers PET concentration distribution images based on stacked autoencoder according to claim 1 characterized in that: in step (4), the test set $\hat{x}$ is input to the concentration distribution image reconstruction model to reconstruct the dynamic PET concentration distribution images of two tracers, the specific process is as follows:

first, each column in the test set $\hat{x} = [\hat{x}_1, \hat{x}_2, \ldots, \hat{x}_{m \times m}]$ is used as the input of stacked autoencoder to obtain the output:

$$ô = [ô_1, ô_2, \ldots, ô_{m \times m}]$$

then ô is decomposed into $\hat{x}^1 = [\hat{x}_1^1, \hat{x}_2^1, \ldots, \hat{x}_{m \times m}^1]$ and $\hat{x}^2 = [\hat{x}_1^2, \hat{x}_2^2, \ldots, \hat{x}_{m \times m}^2]$ to reconstruct dynamic tracer PET concentration distribution images of two tracers.

* * * * *